United States Patent
Jimenez et al.

(10) Patent No.: US 10,884,593 B1
(45) Date of Patent: Jan. 5, 2021

(54) SYSTEMS AND METHODS FOR REMOTE LAYOUT CONTROL OF MEDICAL IMAGE VIEWERS

(71) Applicant: GE Precision Healthcare, LLC, Milwaukee, WI (US)

(72) Inventors: Juan Diego Jimenez, South Jordan, UT (US); Gang Cheng, Sandy, UT (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 0 days.

(21) Appl. No.: 16/696,426

(22) Filed: Nov. 26, 2019

(51) Int. Cl.
| | |
|---|---|
| *G06F 3/0484* | (2013.01) |
| *G06T 11/60* | (2006.01) |
| *G06F 3/0482* | (2013.01) |
| *G06F 3/147* | (2006.01) |
| *G16H 30/40* | (2018.01) |
| *G16H 40/67* | (2018.01) |
| *G16H 30/20* | (2018.01) |

(52) U.S. Cl.
CPC ........ *G06F 3/04845* (2013.01); *G06F 3/0482* (2013.01); *G06F 3/147* (2013.01); *G06T 11/60* (2013.01); *G16H 30/20* (2018.01); *G16H 30/40* (2018.01); *G16H 40/67* (2018.01); *G06F 2203/04803* (2013.01); *G06T 2200/24* (2013.01); *G06T 2210/41* (2013.01)

(58) Field of Classification Search
CPC .... G06F 3/04845; G06F 3/0482; G06F 3/147; G06F 2203/04803; G16H 40/67; G16H 30/20; G16H 30/40; G06T 11/60; G06T 2200/24; G06T 2210/41
See application file for complete search history.

(56) References Cited

U.S. PATENT DOCUMENTS

| | | | | | |
|---|---|---|---|---|---|
| 5,819,278 | A | * | 10/1998 | Hamburg | ................. G06T 11/00 |
| 5,905,506 | A | * | 5/1999 | Hamburg | ................. G06T 11/00 345/672 |
| 5,986,662 | A | * | 11/1999 | Argiro | ..................... G06T 11/00 345/419 |
| 6,016,438 | A | * | 1/2000 | Wakayama | ............. G06T 19/00 324/307 |

(Continued)

OTHER PUBLICATIONS https://www.Brainlab.com/surgery-products/overview-plafform-product/kick-navigation/.
https://www.youtube.com/watch?v=ZyLMyOLGWJU&t=45.

*Primary Examiner* — Jung-Mu T Chuang
(74) *Attorney, Agent, or Firm* — Armstrong Teasdale LLP (57) ABSTRACT

A layout control computing device is provided. The computing device includes a processor programmed to display a control user interface via a first display screen and a display user interface via a second display screen. The control user interface includes a layout template having a plurality of tiles, each tile having an indicator of a render view. The display user interface includes a plurality of viewports arranged according to the layout template, and each viewport is configured to display the medical images in a render view as indicated by an indicator of a corresponding tile. The processor is also programmed to receive a command of moving a first tile to a location of a second tile, update the layout template, instruct to arrange the viewports according to the updated layout template, and instruct to display the images in the viewports in render views as indicated in the updated layout template.

20 Claims, 11 Drawing Sheets

(56) References Cited

U.S. PATENT DOCUMENTS

| | | | | |
|---|---|---|---|---|
| 6,108,573 | A * | 8/2000 | Debbins | G01R 33/54 324/309 |
| 6,224,549 | B1 * | 5/2001 | Drongelen | A61B 5/00 600/300 |
| 6,323,869 | B1 * | 11/2001 | Kohm | G06T 5/009 345/581 |
| 6,411,310 | B1 * | 6/2002 | Berquist | G06Q 10/10 715/764 |
| 6,510,459 | B2 * | 1/2003 | Cronin, III | G06F 16/9577 709/219 |
| 6,578,002 | B1 * | 6/2003 | Derzay | G06F 19/3418 705/2 |
| 6,707,469 | B1 * | 3/2004 | Kelly | G06F 8/38 715/744 |
| 6,724,403 | B1 * | 4/2004 | Santoro | 715/765 |
| 6,803,884 | B1 * | 10/2004 | Ohzawa | G02B 27/0172 345/1.1 |
| 6,915,490 | B1 * | 7/2005 | Ewing | G06F 3/0481 715/794 |
| 7,656,543 | B2 * | 2/2010 | Atkins | H04N 1/00132 358/1.13 |
| 8,020,103 | B2 * | 9/2011 | Fried | G06F 16/954 715/740 |
| 8,504,932 | B2 * | 8/2013 | Quek | G06T 11/60 715/710 |
| 8,599,215 | B1 * | 12/2013 | Boitano | G06T 3/4038 345/419 |
| 8,754,827 | B2 * | 6/2014 | Braghis | G06F 3/1454 345/1.3 |
| 8,837,794 | B2 * | 9/2014 | Nakamura | A61B 5/416 382/128 |
| 8,881,052 | B2 * | 11/2014 | Strauss | G06F 9/451 715/802 |
| 8,913,078 | B2 * | 12/2014 | Masumoto | G06F 19/321 345/619 |
| 8,922,575 | B2 * | 12/2014 | Garside | G06F 3/033 345/557 |
| 9,019,301 | B2 * | 4/2015 | Matsue | G06F 19/321 345/619 |
| 9,110,566 | B2 * | 8/2015 | Kim | G06F 3/04817 |
| 9,164,673 | B2 | 10/2015 | Cheng et al. | |
| 9,262,444 | B2 * | 2/2016 | Gross | G06F 19/321 |
| 9,495,532 | B1 * | 11/2016 | Zhurkin | G06F 21/36 |
| 9,600,158 | B2 * | 3/2017 | Temkin | G06F 3/04845 |
| 9,785,323 | B2 * | 10/2017 | Lu | G06F 3/04845 |
| 10,096,382 | B2 * | 10/2018 | Zhu | G06F 19/321 |
| 10,335,572 | B1 * | 7/2019 | Kumar | G02B 27/017 |
| 10,387,007 | B2 * | 8/2019 | Silva | H04N 5/44591 |
| 10,387,612 | B2 * | 8/2019 | Wu | G16H 40/63 |
| 10,444,960 | B2 * | 10/2019 | Marshall | G06F 3/04845 |
| 2001/0032238 | A1 * | 10/2001 | Cronin, III | G06F 16/9577 709/203 |
| 2006/0103891 | A1 * | 5/2006 | Atkins | H04N 1/00132 358/450 |
| 2007/0242069 | A1 * | 10/2007 | Matsue | G06F 19/321 345/428 |
| 2008/0008401 | A1 * | 1/2008 | Zhu | G06F 19/00 382/294 |
| 2008/0101703 | A1 * | 5/2008 | Shafer | G06K 9/00456 382/203 |
| 2008/0313533 | A1 * | 12/2008 | Hoyer | G06F 40/103 715/243 |
| 2009/0213034 | A1 * | 8/2009 | Wu | G16H 30/20 345/1.1 |
| 2009/0327872 | A1 * | 12/2009 | Kamiyama | G06F 40/166 715/243 |
| 2010/0223568 | A1 * | 9/2010 | Quek | G06T 11/60 715/765 |
| 2011/0026839 | A1 * | 2/2011 | Bogart | G06T 11/60 382/217 |
| 2011/0074656 | A1 * | 3/2011 | Mizuno | G06F 3/1454 345/1.1 |
| 2011/0105879 | A1 * | 5/2011 | Masumoto | G06F 19/321 600/407 |
| 2011/0157227 | A1 * | 6/2011 | Ptucha | H04N 5/232 345/638 |
| 2011/0289423 | A1 * | 11/2011 | Kim | G06F 3/04886 715/741 |
| 2012/0001832 | A1 * | 1/2012 | Braghis | H04N 19/146 345/2.2 |
| 2012/0063655 | A1 * | 3/2012 | Dean | G16H 50/50 382/128 |
| 2012/0131498 | A1 * | 5/2012 | Gross | G06F 16/54 715/788 |
| 2012/0183191 | A1 * | 7/2012 | Nakamura | G06F 19/321 382/128 |
| 2013/0049298 | A1 * | 2/2013 | Andrews | A63F 3/0052 273/267 |
| 2013/0057587 | A1 * | 3/2013 | Leonard | G06F 9/451 345/660 |
| 2013/0063443 | A1 * | 3/2013 | Garside | G06F 3/033 345/473 |
| 2013/0141366 | A1 * | 6/2013 | Ritter | G06F 3/041 345/173 |
| 2013/0239055 | A1 * | 9/2013 | Ubillos | G06F 3/0482 715/815 |
| 2014/0189551 | A1 * | 7/2014 | Kim | G06F 3/04817 715/765 |
| 2014/0245148 | A1 * | 8/2014 | Silva | H04N 21/4126 715/719 |
| 2014/0344700 | A1 * | 11/2014 | Kane | G06F 3/04817 715/726 |
| 2015/0199117 | A1 * | 7/2015 | Zalewski | G06F 3/03547 715/765 |
| 2015/0253963 | A1 * | 9/2015 | Koohestanian | G06F 3/0486 715/745 |
| 2016/0026371 | A1 * | 1/2016 | Lu | G06F 3/04886 715/765 |
| 2017/0177794 | A1 * | 6/2017 | Dorn | G06F 19/321 |
| 2017/0296932 | A1 * | 10/2017 | Kushner | A63F 13/33 |
| 2017/0329922 | A1 * | 11/2017 | Eberting | G16H 10/60 |
| 2018/0113575 | A1 * | 4/2018 | Rakotoarivony | G06F 3/0486 |
| 2019/0214116 | A1 * | 7/2019 | Eberting | G16H 50/30 |

* cited by examiner

SYSTEMS AND METHODS FOR REMOTE LAYOUT CONTROL OF MEDICAL IMAGE VIEWERS

BACKGROUND

The field of the disclosure relates generally to systems and methods of remote layout control of image viewers, and more particularly, to systems and methods of remotely controlling layout of displaying medical images in multiple render views.

Medical images of the anatomy of a patient in various render views or perspectives are provided so that a physician can view the anatomy from various perspectives or angles. Physicians may have different preferences to the various render views and may also want to focus on a certain render view while other render views are simultaneously presented on a display screen. When all of the various render views are displayed on a large display screen, it may not be convenient for a user to move a viewport of a render view to a desired location on the screen. Further, medical images have been used in an operating room to assist surgeons in surgery. During surgery, there are multiple monitors and control screens in the operating room. A system that allows the surgeon to instruct a technician to remotely and intuitively modify the layout of the viewports via a control user interface is needed.

BRIEF DESCRIPTION

In one aspect, a layout control computing device for use in controlling a layout of displaying medical images in a plurality of render views is provided. The computing device includes at least one processor electrically coupled to at least one memory device, the at least one processor programmed to display, via a first display screen, a control user interface, wherein the control user interface includes a layout template having a plurality of tiles, each tile having an indicator of a render view in which the medical images will be displayed. The at least one processor is further programmed to display, via a second display screen, a display user interface, wherein the display user interface includes a plurality of viewports arranged according to the layout template, and each viewport is configured to display the medical images in a render view as indicated by an indicator of a corresponding tile. The at least one processor is also programmed to receive, from the control user interface, a command of moving a first tile to a location of a second tile, update the layout template by swapping a location of the first tile with the location of the second tile, and instruct to arrange the viewports according to the updated layout template. The at least one processor is further programmed to instruct to display, via the display user interface, the medical images in the viewports in render views as indicated by indicators of corresponding tiles in the updated layout template.

In another aspect, a computer-enabled system for controlling a layout of displaying medical images in a plurality of render views is provided. The system includes a first display screen, a second display screen, a control user interface, a display user interface, and a layout computing device. The control user interface is displayed on the first display screen, the control user interface including a layout template having a plurality of tiles, each tile having an indicator of a render view in which the medical images will be displayed. The display user interface is displayed on the second display screen, the display user interface being in communication with the control user interface and including a plurality of viewports arranged according to the layout template, and each viewport configured to display the medical images in a render view as indicated by an indicator of a corresponding tile. The layout control computing device includes at least one processor electrically coupled to at least one memory device, the layout control computing device being in communication with the first display screen, the second display screen, the control user interface and the display user interface. The at least one processor is programmed to receive, from the control user interface, a command of moving a first tile to a location of a second tile, update the layout template by swapping a location of the first tile with the location of the second tile, and instruct to arrange the viewports according to the updated layout template. The at least one processor is further programmed to instruct to display, by the display user interface, the medical images in the viewports in render views as indicated by indicators of corresponding tiles in the updated layout template.

In yet another aspect, a computer-implemented method for controlling a layout of displaying medical images in a plurality of render views is provided. The method includes displaying, via a first display screen, a control user interface, wherein the control user interface includes a layout template, and the layout template includes a plurality of tiles, each tile having an indicator of a render view in which the medical images will be displayed. The method also includes displaying, via a second display screen, a display user interface, wherein the display user interface includes a plurality of viewports arranged according to the layout template, and each viewport is configured to display the medical images in a render view as indicated by an indicator of a corresponding tile. The method further includes receiving, from the control user interface, a command of moving a first tile to a location of a second tile, updating the layout template by swapping a location of the first tile with the location of the second tile, and arranging the viewports according to the updated layout template. Moreover, the method includes displaying, via the display user interface, the medical images in the viewports in render views as indicated by indicators of corresponding tiles in the updated layout template.

DETAILED DESCRIPTION

The disclosure includes systems and methods for controlling the layout of displaying medical images in multiple render views. In medical imaging, a three-dimensional (3D) volume of medical images are medical images of a volume of the anatomy in a patient. The 3D volume of medical images may be acquired and/or displayed in various render views, such as sagittal, axial, and coronal views. In x-ray imaging, a series of images may be acquired along an anterior-posterior perspective, where the images are acquired as if a camera were aimed from the front of the patient toward the back of the patient. The resulting images may be labeled as having a render view of anterior-posterior (AP). Images may also be acquired along a lateral perspective where the images are acquired as if a camera was aimed from a side of the patient. Further, the resulting images may be labeled as having a render view of lateral or LAT for short. Once a 3D volume of medical images are acquired, volume rendering of the medical images may be generated based on the acquired medical images. A volume rendering of medical images shows the medical images in a 3D perspective, instead of a series of two-dimensional (2D) images. It is desirable that image display application of medical images allow a user to choose which render views to display and to conveniently and intuitively change the layout of the viewports displaying medical images in those render views.

Figure 1:
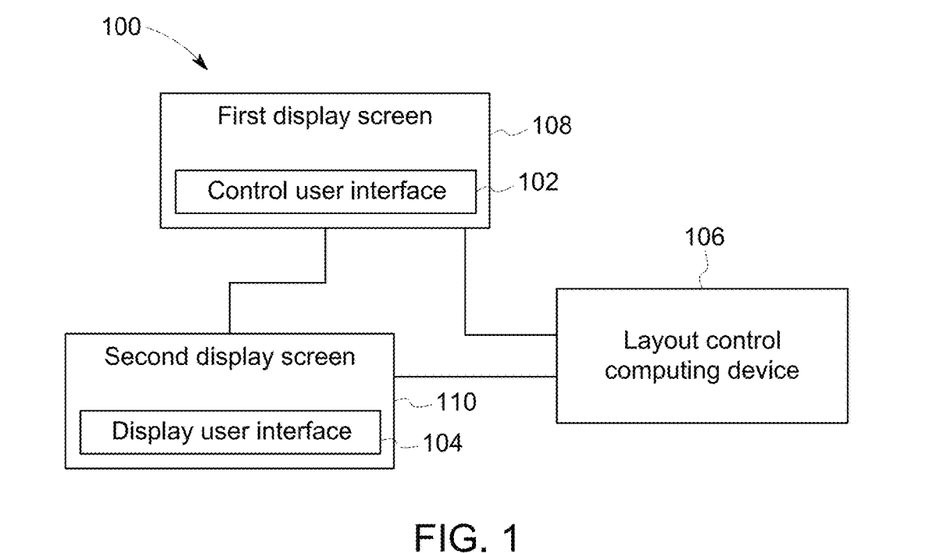
FIG. 1 is a schematic diagram of an exemplary layout control system.

FIG. 1 is a schematic diagram of an exemplary computer-enabled system 100 for controlling a layout of displaying medical images in a plurality of render views. System 100 includes a control user interface 102, a display user interface 104, and a layout control computing device 106. Control user interface 102 is displayed on a first display screen 108. Display user interface 104 is displayed on a second display screen 110. First and second display screens 108, 110 may be the same screen or separate screens, and may be controlled by separate computing devices or the same computing device. Control user interface 102 is configured to control the layout of viewports 212a, 212b, 312a, 312b, 412a, 412b, 412c (shown in FIGS. 2B, 3B, and 4B) for displaying images on display user interface 104. In operation, layout control computing device 106 is in communication with and controls control user interface 102 and display user interface 104.

Figure 2A:
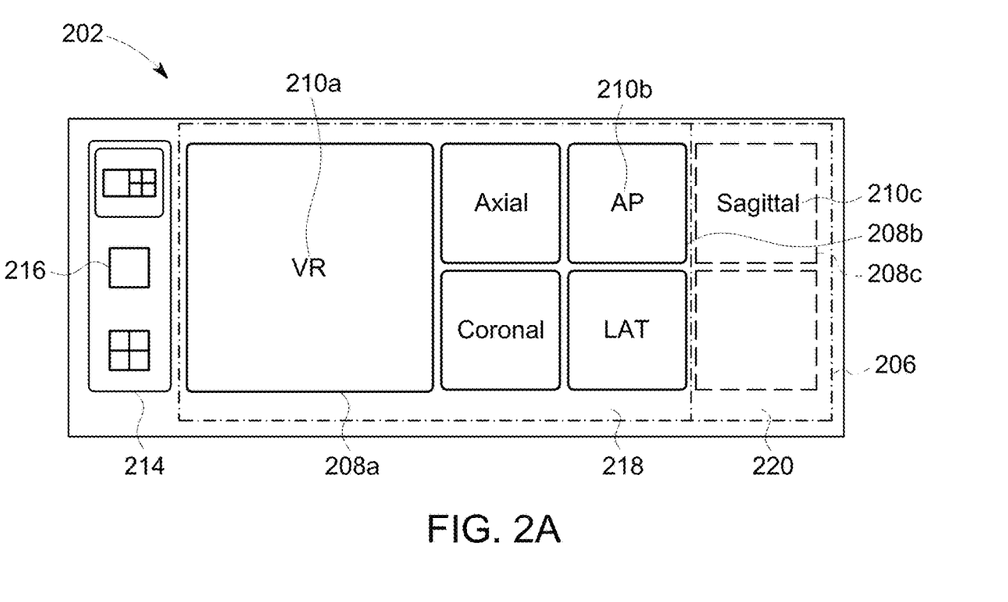
FIG. 2A is an exemplary control user interface of the system shown in FIG. 1.
Figure 2B:
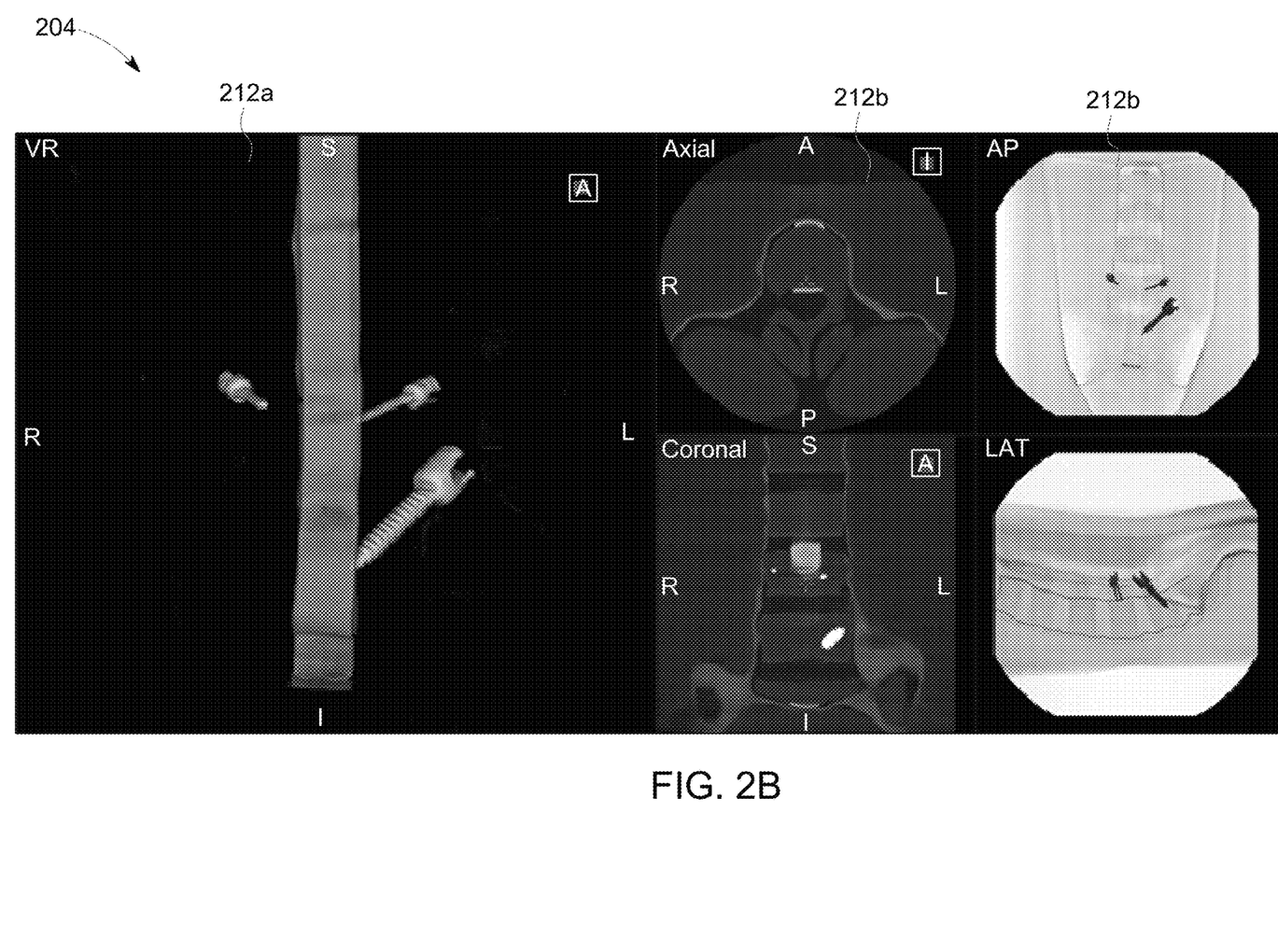
FIG. 2B is an exemplary display user interface controlled by the control user interface shown in FIG. 2A.

FIG. 2A illustrates an exemplary control user interface 202. In the exemplary embodiment, control user interface 202 is similar to control user interface 102 shown in FIG. 1. FIG. 2B illustrates an exemplary display user interface 204. In the exemplary embodiment, display user interface 204 is similar to display user interface 104. Display user interface 204 includes a plurality of viewports 212a, 212b. Control user interface 202 includes a layout template 206. Layout template 206 includes one or more tiles 208a, 208b. Tiles may be in various dimensions. For example, tile 208a has greater dimensions than tile 208b. The relative dimensions of tiles and their corresponding viewports are kept the same. That is, tile 208a has larger dimensions than tile 208b, and viewport 212a corresponding to viewport 208a has larger dimensions than viewport 212b corresponding to tile 208b. A larger viewport 212a may be used to show the images in the render view that a user is more interested in. Tiles 208a, 208b have indicators 210a, 210b that indicate the render view of images displayed in corresponding viewport 212a, 212b. For example, indicator 210a may be "VR," which stands for volume rendering and is used to indicate volume rendering and the images shown in viewport 212a are volume rendering of the medical images. Indicator 210b may be "AP" that is used to indicate that images were acquired along the anterior-posterior perspective of the patient, and that images shown in viewport 212b are those images shown along that render view.

In the exemplary embodiment, control user interface 202 may further include a menu 214 of layout templates 206. Menu 214 includes a list of layout templates 206. In FIG. 2A, three layout templates 206 are shown and available to a user. Menu 214 may also include a plurality of buttons 216, with each button corresponding to a layout template 206. A user may click or touch button 216 to choose a desirable layout template 206. Alternatively, menu 214 may be a pull-down menu (not shown), where a user may expand the menu to choose a layout template 206. In the exemplary control user interface 202 shown in FIG. 2A, a button 216 at the top of menu 214 is chosen, which corresponds to a layout having one tile 208a and four tiles 208b.

In some embodiments, layout template 206 may include an active portion 218 and an inactive portion 220. Active portion 218 includes active tiles 208a, 208b corresponding active viewports 212a, 212b. Inactive portion 220 includes inactive tiles or parking lots 208c. In display user interface 204, images are not shown at locations corresponding to inactive tiles 208c. Inactive tile 208c may further include an indicator 210c. Inactive tiles 208c may be marked with dashed outlines to indicate they are inactive.

FIG. 2B shows the exemplary display user interface 204 corresponding to layout template 206 prescribed by a user in control user interface 202 as shown in FIG. 2A. Display user interface 204 includes a plurality of viewports 212a, 212b. In the exemplary display user interface 204, medical images of a patient are shown in five viewports 212 in render views as indicated on tiles 208a, 208b, e.g., VR, Axial, Coronal, AP, and LAT render views (clockwise in FIG. 2A), which means the images will be shown in render views of volume rendering, axial, coronal, anterior-posterior, and lateral. Viewports 212 are arranged according to layout template 206. For example, layout template 206 shows a VR tile 208a with tiles 208b in a two-by-two formation to one side of tile 208a. Correspondingly, viewports 212 are arranged as a VR viewport 212a having two-by-two viewports 212b arranged to its right and viewport 212a having greater dimensions than viewports 212b. Viewport 212a shows a volume rendering of the images, and viewports 212b show axial, anterior-posterior, lateral, coronal render views of the images (clockwise in FIG. 2B).

In operation, control user interface 202 controls the locations and render views of viewports 212a, 212b in display user interface 204. A user controls the layout of the viewports 212a, 212b through control user interface 202. Control user interface 202 has much smaller dimensions than display user interface 204 and has indicators 210a, 210b of render views presented on tiles 208a, 208b, which allows easy and intuitive maneuvering. Control user interface 202 and display user interface 204 may be provided on separate computing devices, separate display screens controlled by the same computing device, or the same display screen.

Figure 3A:
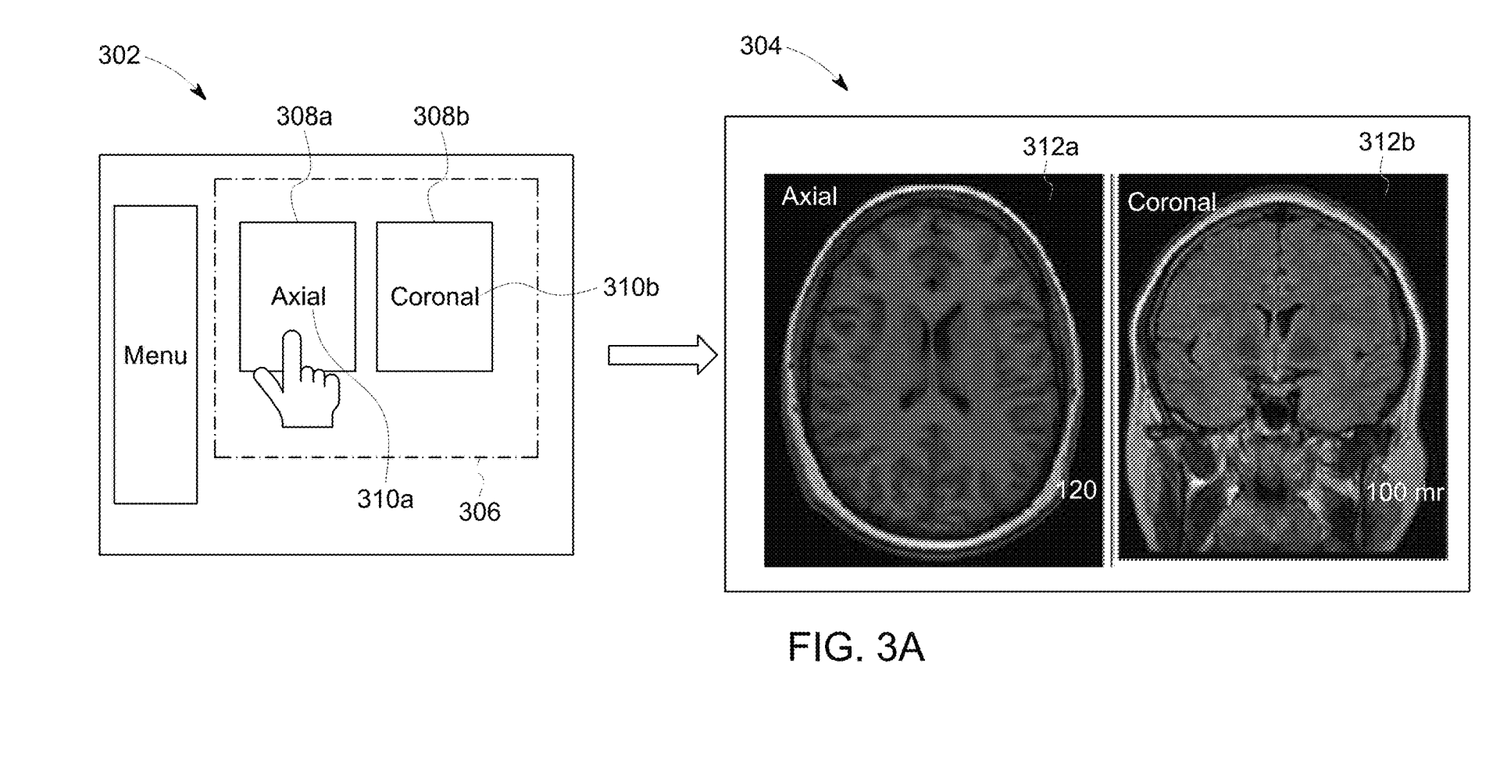
FIG. 3A is a schematic diagram showing an exemplary control user interface and its corresponding display user interface before a user moves a tile in the control user interface.
Figure 3B:
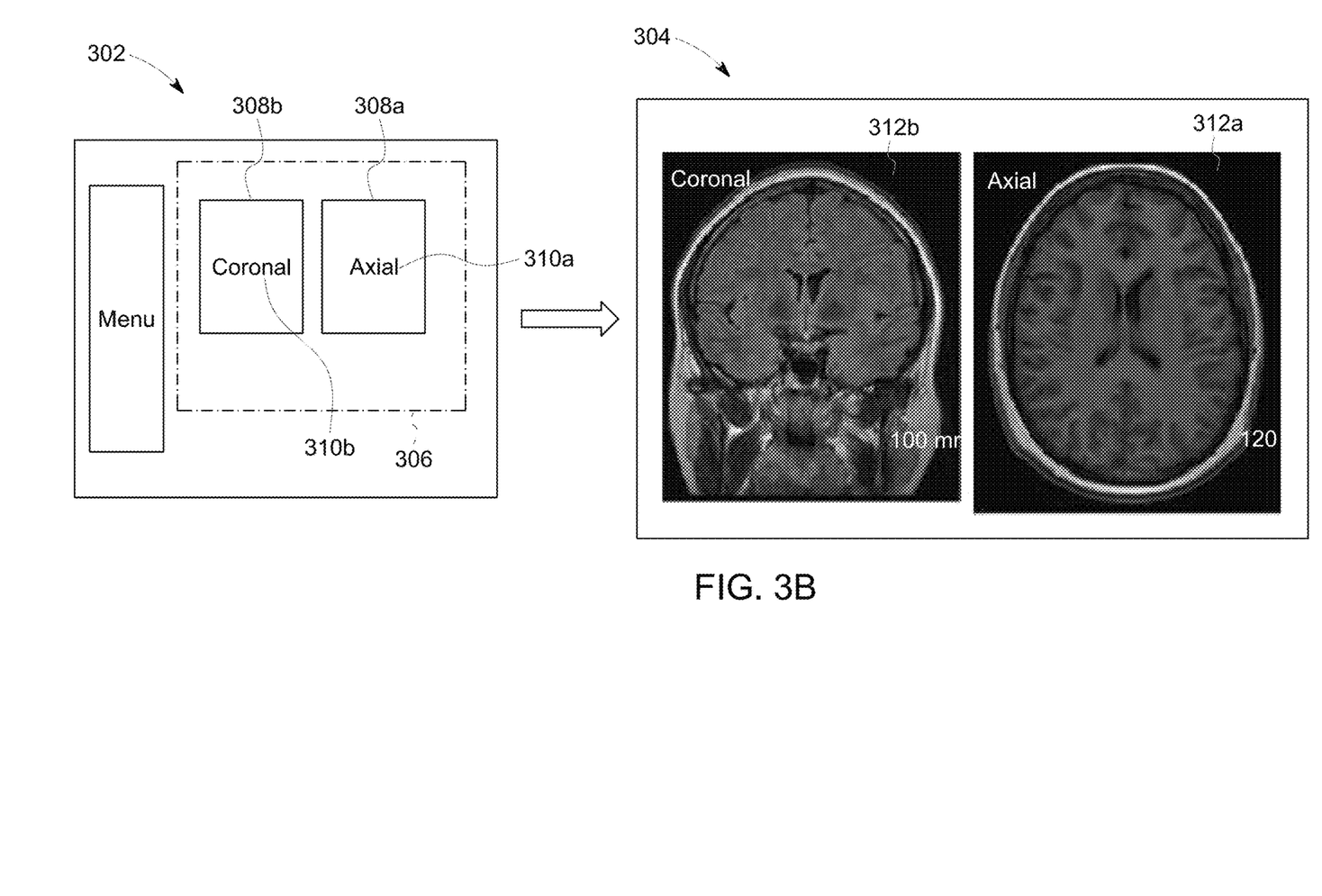
FIG. 3B is a schematic diagram showing the control user interface and the display user interface shown in FIG. 3A after the user moves the tile in the control user interface.

FIGS. 3A and 3B show an exemplary control user interface 302 that is being used to control and modify the layout of viewports 312a, 312b in display user interface 304. FIG. 3A shows control user interface 302 and display user interface 304 before a user moves tile 308a and FIG. 3B shows control user interface 302 and display user interface 304 after the move. The exemplary medical images are brain images of a patient. In FIG. 3A, control user interface 302 has a layout template 306 with tiles 308a, 308b being horizontally aligned to each other and tile 308a positioned to the left of tile 308b. In display user interface 304, viewports 312a, 312b are arranged according to layout template 306, i.e., viewports 312a, 312b are side-by-side next to each other and viewports 312a being positioned to the left of viewport 312b. Tiles 308a, 308b have indicators 310a, 310b indicating the views of their corresponding viewports 312a, 312b. In the exemplary control interface 302, tile 308a has indicator 310a of axial and tile 308b has indicator 310b of coronal. Their corresponding viewports 312a, 312b show an axial view and a coronal view of the brain, respectively.

In the exemplary embodiment, a user may move tiles 308a, 308b. For example, a user may choose tile 308a by a mouse click or a direct touch and drag and drop it over tile 308b. As a result, tiles 308a, 308b swap their locations in layout template 306 (FIG. 3B), i.e., the locations of tiles 308a, 308b are exchanged. Viewports 312a, 312b are arranged according to the updated layout template 306 with viewport 312a swapped position with viewport 312b (FIG. 3B). In display user interface 304, a coronal view of brain is shown in viewport 312b to the left of the axial view in viewport 312a. If a user drops tile 308a out of the boundary of layout template 306, tile 308a will return to its original location. If the user drags but releases tile 308a back to its original location, the location of tile 308a in layout template 306 will not change. In both scenarios, no changes will be made to layout of display user interface 304 as layout template 306 has not been changed.

Figure 4A:
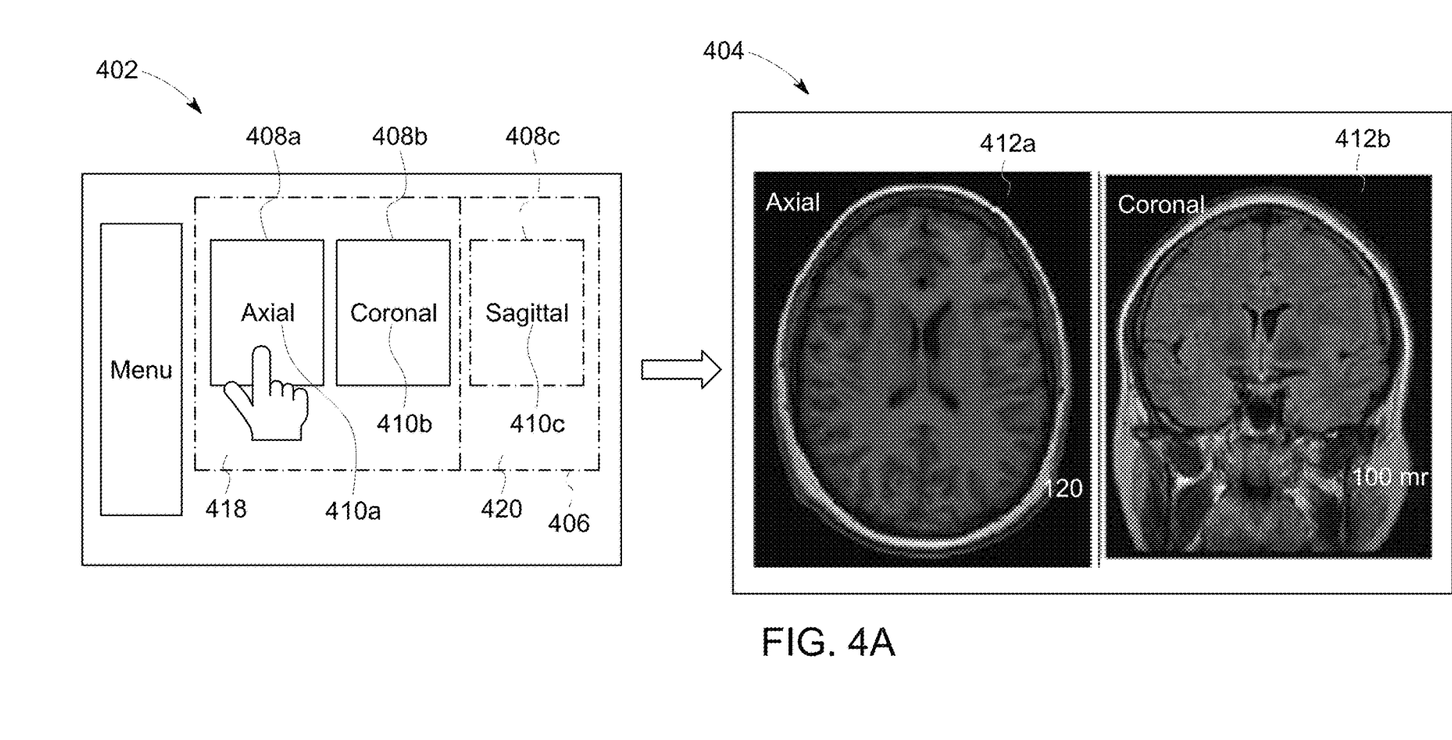
FIG. 4A is a schematic diagram showing an exemplary control user interface having an inactive portion and its corresponding display user interface before a user moves a tile in the control user interface.
Figure 4B:
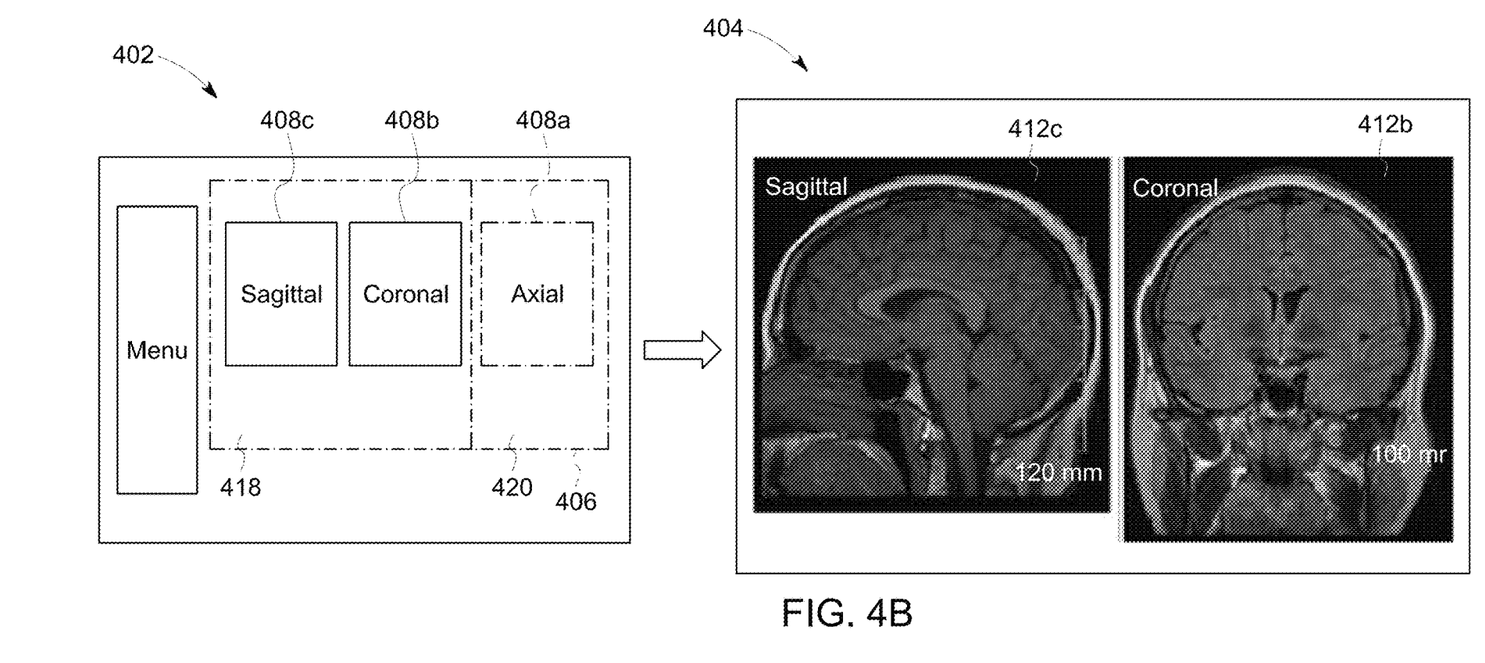
FIG. 4B is a schematic diagram showing the control user interface and the display user interface shown in FIG. 4A after the user moves the tile in the control user interface.

FIGS. 4A and 4B show an exemplary control user interface 402 including an inactive portion 420 in layout template 406 and being used to control and modify the layout of viewports 412a, 412b, 412c in display user interface 404. FIG. 4A shows control user interface 402 and display user interface 404 before a user moves tile 408a to inactive portion 420 and FIG. 4B shows control user interface 402 and display user interface 404 after the move. Control user interface 402 includes a layout template 406 having an active portion 418 and inactive portion 420. Active portion 418 includes active tiles 408a, 408b with tile 408a positioned to the left of tile 408b. Tiles 408a, 408b have indicators 410a, 410b as Axial and Coronal, respectively. Inactive portion 420 includes an inactive tile 408c with an indicator 410c as Sagittal. In a display user interface 404, viewports 412a, 412b are arranged according to active portion 418 of layout template 406. In comparison, a sagittal view of the brain is not shown to the user, as tile 408c is inactive. When a user drags tile 408a and drops it over tile 408c, the locations of these two tiles 408a, 408c are swapped (FIG. 4B). As a result, active portion 418 now includes tile 408c and 408b with tile 408c positioned to the left of tile 408b, and inactive portion 420 now includes tile 408a. Correspondingly, in display user interface 404, viewports 412c, 412b show images in sagittal and coronal views as indicated by the indicators 410c, 410b of their corresponding tiles 408c, 408a. An axial view is not shown as tile 408a now becomes inactive.

Figure 5A:
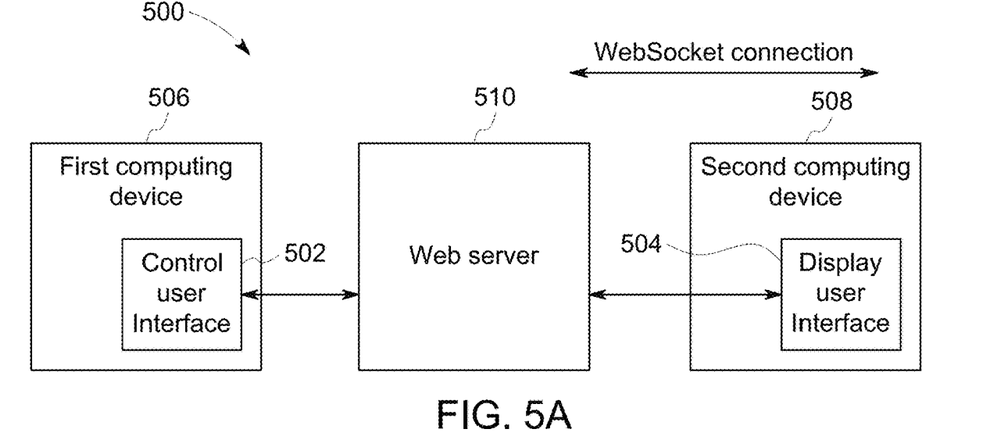
FIG. 5A is a block diagram of an exemplary system shown in FIG. 1 including separate computing devices.
Figure 5B:
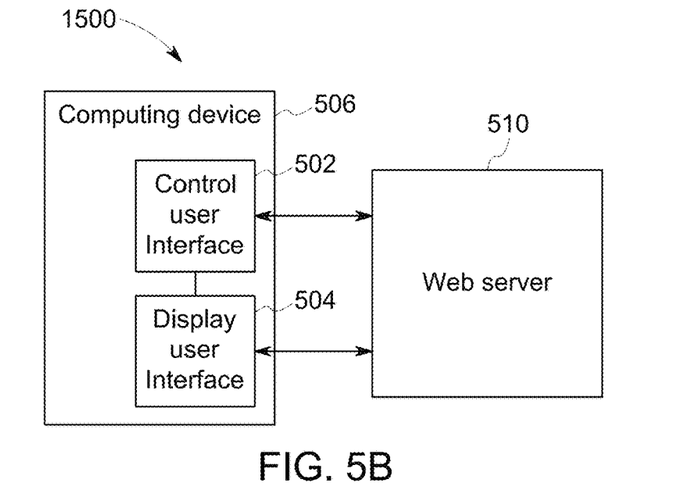
FIG. 5B is a block diagram of another exemplary system shown in FIG. 1 with its control and display user interfaces implemented on the same computing device.
Figure 5C:
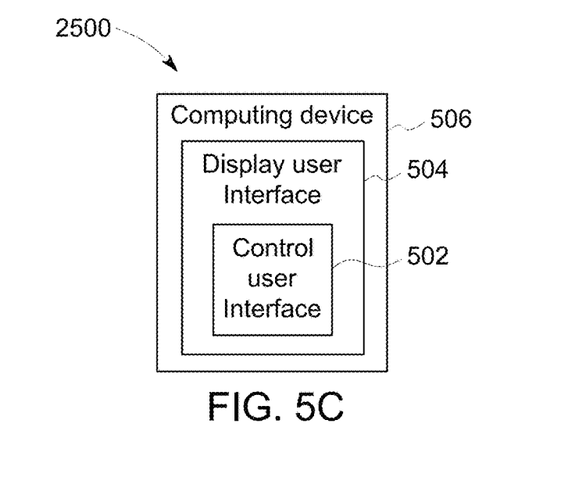
FIG. 5C is a block diagram of one more exemplary system shown in FIG. 1 with its control and display user interfaces implemented on the same computing device in one application.

FIGS. 5A-5C show various exemplary systems 500, 1500, 2500 for controlling a layout of displaying medical images in a plurality of views. For example, system 500 includes a control user interface 502 and a display user interface 504. Control user interface 502 is similar to control user interface 102, 202, 302, 402 shown in FIGS. 1, 2A, and 3A-4B. Display user interface 504 is similar to display user interface 104, 204, 304, 404 shown in FIGS. 1, 2B, 3A-4B. Control user interface 502 and display user interface 504 are provided on first and second computing devices 506, 508, respectively. Control user interface 502 and display user interface 504 communicate with each other through a web server 510. The communication may be conducted through a WebSocket connection.

In another example, in system 1500, control user interface 502 and display user interface 504 are provided on one computing device 506. Control user interface 502 and display user interface 504 may be displayed on separate display screens controlled by computing device 506 or may be displayed on the same display screen. Control user interface 502 and display user interface 504 may both communicate with web server 510 and may also communicate with each other through internal communication channels of computing device 506. In a third example, in system 2500, control user interface 502 is provided within display user interface 504 in one viewer application on the same computing device 506.

Figure 6A:
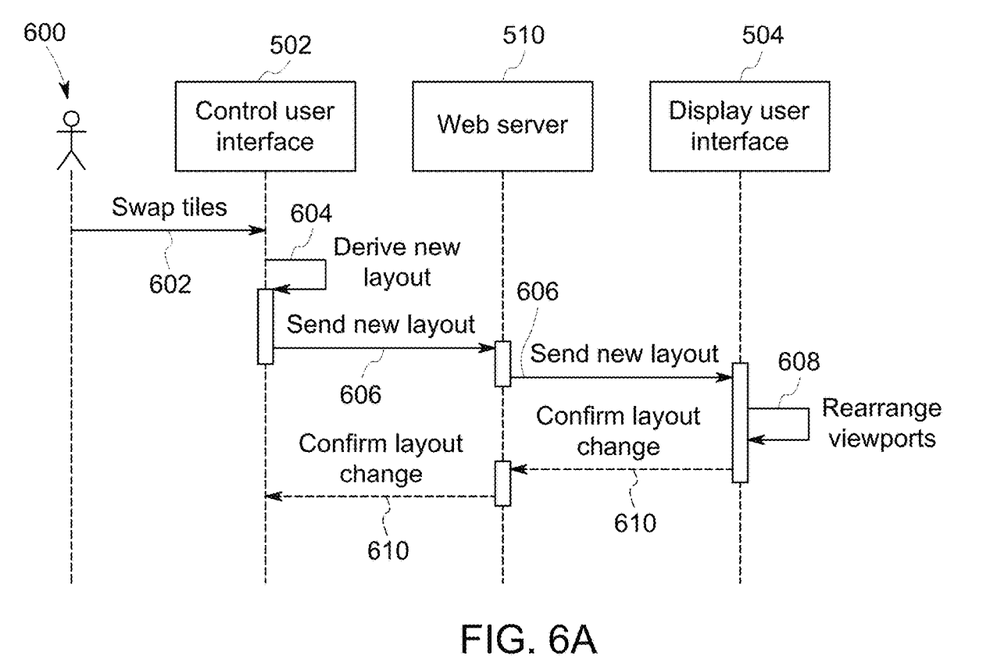
FIG. 6A is a sequence diagram of an exemplary process for swapping viewports in the systems shown in FIGS. 5A and 5B.
Figure 6B:
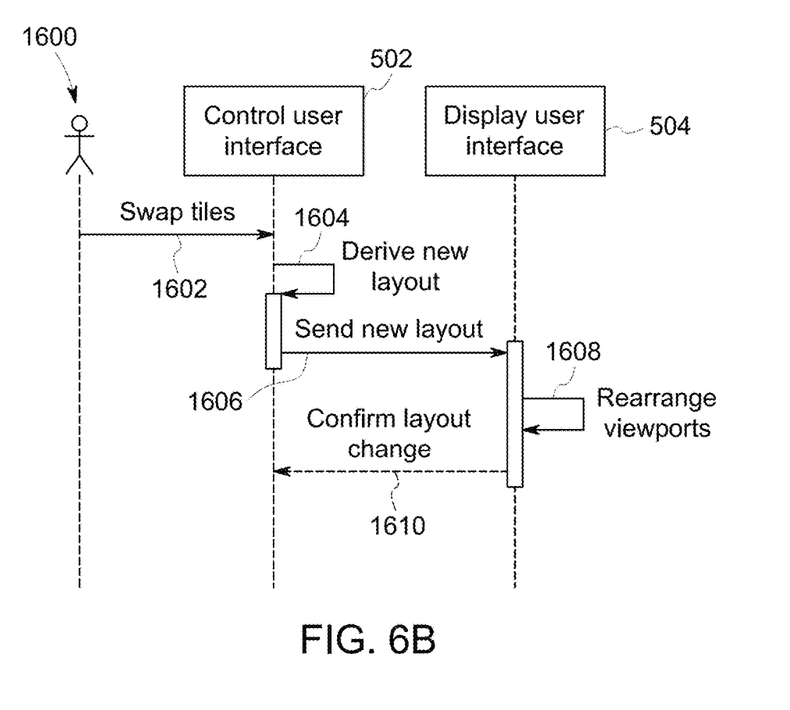
FIG. 6B is a sequence diagram of an exemplary process for swapping viewports in the system shown in FIG. 5C.

FIGS. 6A and 6B show exemplary respective sequence diagrams 600, 1600 for systems 500, 1500, 2500 to carry out the function of swapping viewports on display user interface 504. FIG. 6A shows sequence diagram 600 for system 500, 1500 when control user interface 502 communicates with display user interface 504 through web server 510. FIG. 6B shows sequence diagram 1600 for system 2500.

In the exemplary embodiment, system 500, 1500 includes control user interface 502, web server 510, and display user interface 504. In sequence 600, tiles are first swapped 602 in the control user interface. A new layout is derived 604 in the control user interface. The new layout is then sent 606 out from control user interface through the web server to the display user interface. Viewports are rearranged 608 in the display user interface according to the new layout. The display user interface then sends 610 a confirmation that the layout of the viewports has been changed through the web server to the control user interface.

In sequence 1600, tiles are first swapped 1602 in the control user interface. A new layout is derived 1604 in the control user interface. The new layout is sent 1606 to the display user interface. Once the new layout is received, viewports are rearranged 1608 in the display user interface according to this new layout. The display user interface then sends 1610 a confirmation that the layout of its viewports has been changed. In system 2500, control user interface 502 and display user interface 504 communicate directly with each other.

Figure 7:
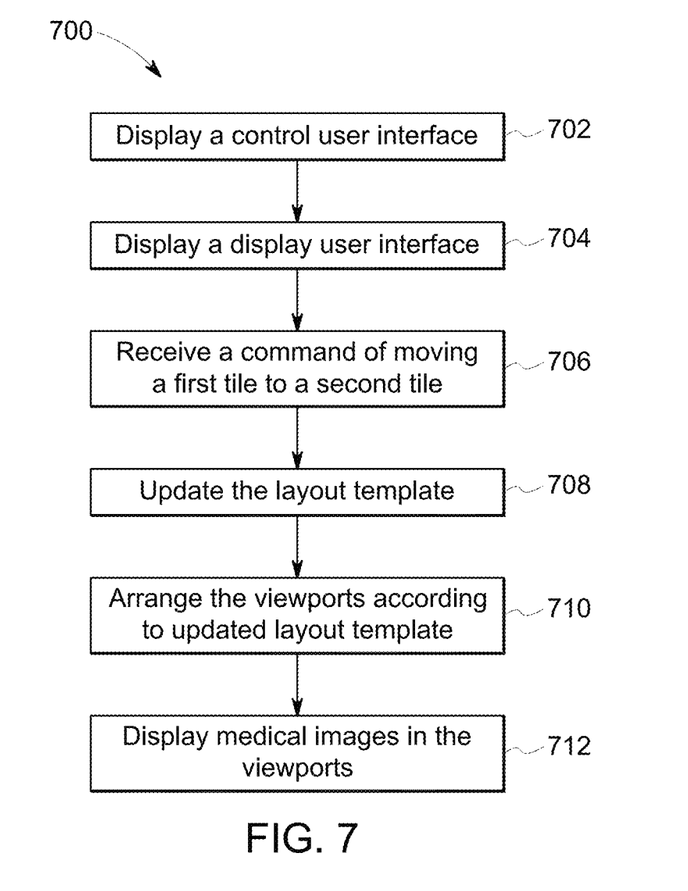
FIG. 7 is an exemplary flowchart for an exemplary method of controlling layout for displaying medical images.

FIG. 7 shows a flow chart of an exemplary method 700 for controlling a layout of displaying medical images in a plurality of render views. Method 700 includes displaying 702, via a first display screen, a control user interface. The control user interface includes a layout template having a plurality of tiles, each tile having an indicator of a render view that the medical images will be displayed. Method 700 further includes displaying 704, via a second display screen, a display user interface. The second display screen may be the same as the first display screen or may be separate from the first display screen. The display user interface includes a plurality of viewports arranged according to the layout template, and each viewport is configured to display the medical images in a render view as indicated by an indicator of a corresponding tile. Method 700 also includes receiving 706, from the control user interface, a command of moving a first tile to a location of a second tile. Further, method 700 includes updating 708 the layout template by swapping the location of the first tile with the location of the second tile. Moreover, method 700 includes arranging 710 the viewports according to the updated layout template. Further, method 700 includes displaying 712, via the display user interface, the medical images in the viewports in views as indicated by indicators of corresponding tiles in the updated layout template.

Figure 8:
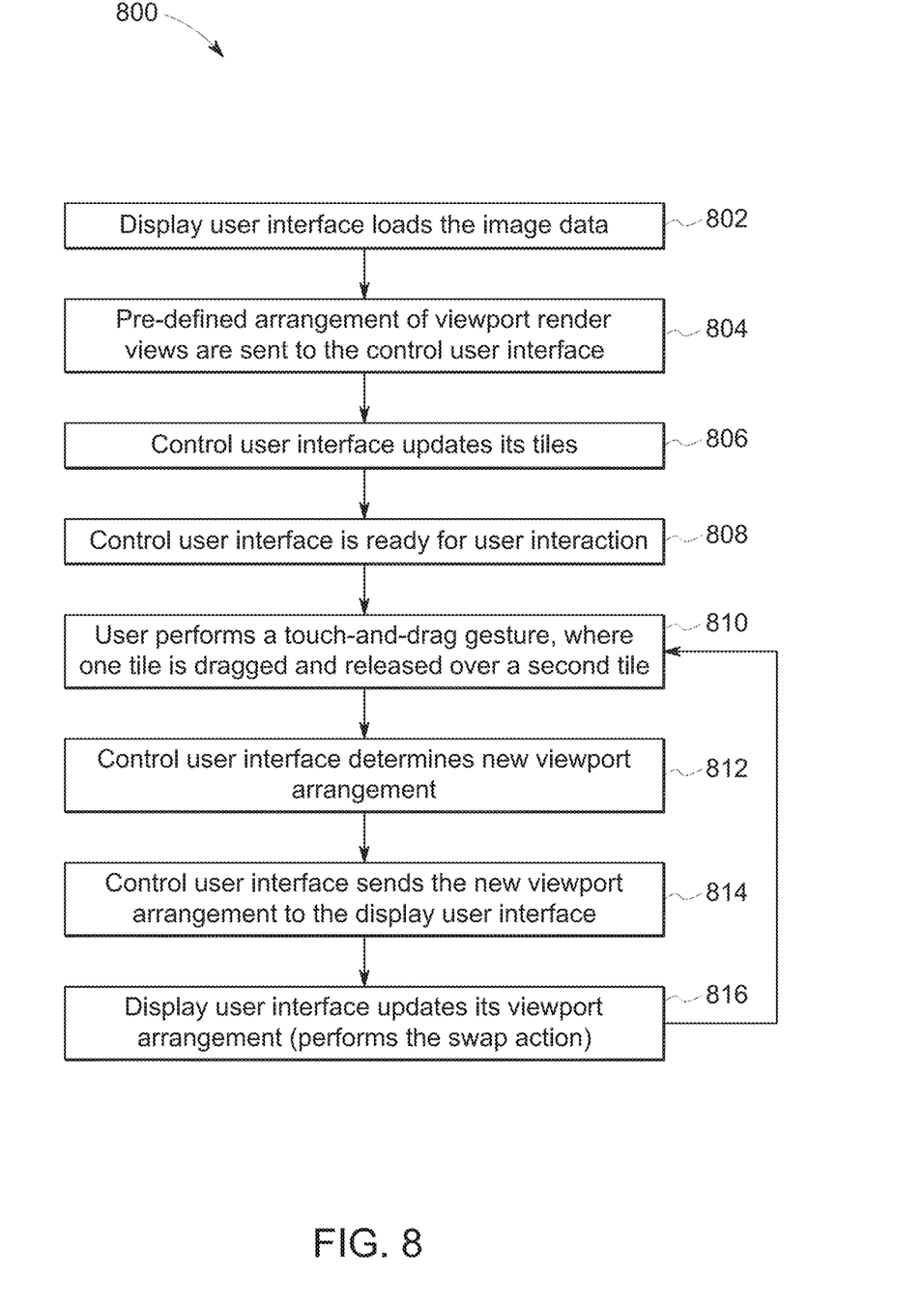
FIG. 8 is an exemplary flow chart for another exemplary method of controlling layout for displaying medical images.

FIG. 8 shows an exemplary flow chart of another exemplary method 800 of controlling viewport layout through a control user interface. A display user interface first loads 802 image data. Pre-defined arrangement of viewport render views are sent 804 to a control user interface. Control user interface then updates 806 its tiles in the layout template. Control user interface is then ready 808 for user interaction. A user performs 810 a touch-and-drag gesture where one tile is dragged and released over a second tile. After this gesture, control user interface determines 812 a new viewport arrangement. Control user interface sends 814 this new viewport arrangement to the display user interface. The display user interface updates 816 its viewport arrangement by performing viewport swapping. The process of viewport rearrangement may be repeated from a user performing 810 to the display user interface updating 816 to carry out the user's various commands.

Figure 9:
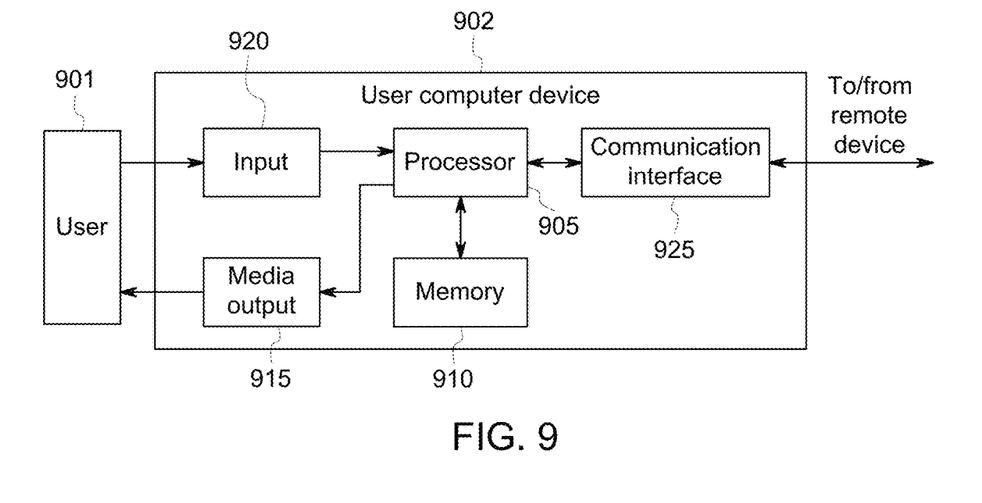
FIG. 9 is a block diagram of an exemplary user computing device.

FIG. 9 illustrates an exemplary configuration of a user computer device 902 operated by a user 901. User computer device 902 may include, but is not limited to, computing devices 506, 508 shown in FIGS. 5A-5C.

User computer device 902 includes a processor 905 for executing instructions. In some embodiments, executable instructions are stored in a memory area 910. Processor 905 may include one or more processing units (e.g., in a multi-core configuration). Memory area 910 is any device allowing information such as executable instructions and/or image data to be stored and retrieved. Memory area 910 may include one or more computer readable media.

User computer device 902 also includes at least one media output component 915 for presenting information to user 901. Media output component 915 is any component capable of conveying information to user 901. In some embodiments, media output component 915 includes an output adapter (not shown) such as a video adapter and/or an audio adapter. An output adapter is operatively coupled to processor 905 and operatively coupleable to an output device such as a display device (e.g., a cathode ray tube (CRT), liquid crystal display (LCD), light emitting diode (LED) display, or "electronic ink" display) or an audio output device (e.g., a speaker or headphones). In some embodiments, media output component 915 is configured to present a graphical user interface (e.g., control user interface 202, 302, 402, 502, display user interface 204, 304, 404, 504, a web browser and/or a client application) to user 901.

In some embodiments, user computer device 902 includes an input device 920 for receiving input from user 901. User 901 may use input device 920 to select and/or enter, without limitation, tiles 208a, 208b, 308a, 308b, 408a, 408b, 408c or layout templates 206. Input device 920 may include, for example, a keyboard, a pointing device, a mouse, a stylus, a touch sensitive panel (e.g., a touch pad or a touch screen), a gyroscope, an accelerometer, a position detector, a biometric input device, and/or an audio input device. A single component such as a touch screen may function as both an output device of media output component 915 and input device 920.

User computer device 902 may also include a communication interface 925, which is communicatively coupleable to a remote device such as web server 510. Communication interface 925 may include, for example, a wired or wireless network adapter and/or a wireless data transceiver for use with a mobile telecommunications network. Stored in memory area 910 are, for example, computer readable instructions for providing a user interface to user 901 via media output component 915 and, optionally, receiving and processing input from input device 920.

Figure 10:
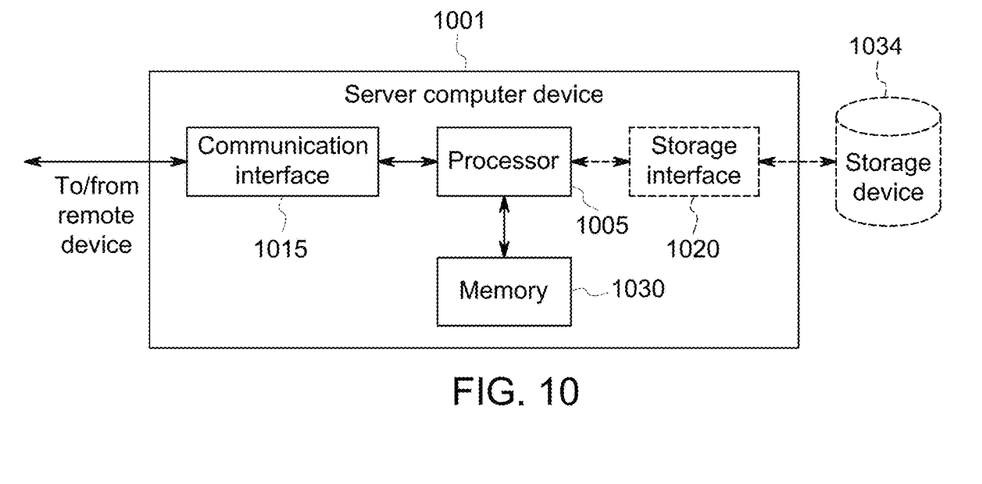
FIG. 10 is a block diagram of an exemplary server computing device.

FIG. 10 illustrates an exemplary configuration of a server computer device 1001 such as web server 510 (shown in FIGS. 5A, 5B, and 6A). Server computer device 1001 also includes a processor 1005 for executing instructions. Instructions may be stored in a memory area 1030, for example. Processor 1005 may include one or more processing units (e.g., in a multi-core configuration).

Processor 1005 is operatively coupled to a communication interface 1015 such that server computer device 1001 is capable of communicating with a remote device such as user computing device 902 or another server computer device 1001. For example, communication interface 1015 may receive requests from user computer device 902 via the Internet.

Processor 1005 may also be operatively coupled to a storage device 1034. Storage device 1034 is any computer-operated hardware suitable for storing and/or retrieving data, such as, but not limited to, 3D volumes of medical images. In some embodiments, storage device 1034 is integrated in server computer device 1001. For example, server computer device 1001 may include one or more hard disk drives as storage device 1034. In other embodiments, storage device 1034 is external to server computer device 1001 and may be accessed by a plurality of server computer devices 1001. For example, storage device 1034 may include multiple storage units such as hard disks and/or solid state disks in a redundant array of inexpensive disks (RAID) configuration. Storage device 1034 may include a storage area network (SAN) and/or a network attached storage (NAS) system.

In some embodiments, processor 1005 is operatively coupled to storage device 1034 via a storage interface 1020. Storage interface 1020 is any component capable of providing processor 1005 with access to storage device 1034. Storage interface 1020 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1005 with access to storage device 1034.

At least one technical effect of the systems and methods described herein includes (a) remote control of a layout for displaying medical images in multiple render views; (b) easy modification of a layout through tiles of relatively small dimensions; (c) increased flexibility of the layout and increased efficiency in use of the display screen by providing inactive tiles and function of swapping tiles into and out of the active portion of the layout template.

Exemplary embodiments of systems and methods of controlling layout for display medical images are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A layout control computing device for use in controlling a layout of displaying medical images in a plurality of render views, said computing device comprising at least one processor electrically coupled to at least one memory device, and said at least one processor programmed to:
    display, via a first display screen, a control user interface configured to control the layout of displaying the medical images in the plurality of render views in a second display screen, wherein the control user interface includes a menu listing one or more layout templates and a layout template selected by a user from the one or more layout templates, the layout template having a plurality of tiles, each tile having an indicator of a render view, wherein the render view is a perspective in which one of the medical images will be displayed, and the layout template does not display the medical images;
    display, via the second display screen, a display user interface configured to display the same medical images in a plurality of perspectives, wherein the display user interface includes a plurality of viewports arranged according to the layout template, and each viewport is configured to display one of the same medical images in a perspective as indicated by a perspective indicator of a corresponding tile;
    receive, from the control user interface, a command by the user of moving a first tile to a location of a second tile in the layout template;
    update the layout template by swapping a location of the first tile with the location of the second tile in response to the command;
    instruct to arrange the viewports of the display user interface according to the updated layout template; and
    instruct to display, via the display user interface, the same medical images in the rearranged viewports in perspectives as indicated by perspective indicators of corresponding tiles in the updated layout template.

2. The computing device of claim 1, wherein said at least one processor is further programmed to:
    receive, from the control user interface, a chosen layout template among the list of layout templates in the menu;
    display the chosen layout template on the control user interface at a location different from a location of the menu;
    arrange the viewports according to the chosen layout template; and
    display, by the display user interface, the medical images in the viewports in as indicated by indicators of corresponding tiles in the chosen layout template.

3. The computing device of claim 1, wherein said at least one processor is further programmed to:
    display, via the control user interface, the layout template including an active portion and an inactive portion, wherein the active portion includes active tiles and the inactive portion includes an inactive tile;
    arrange the viewports according to the active portion of the layout template; and
    display, via the display user interface, the medical images in the viewports in perspectives as indicated by indicators of corresponding tiles in the active portion of the layout template.

4. The computing device of claim 3, wherein said at least one processor is further programmed to:
    receive, from the control user interface, a command by the user of moving an inactive tile to a location of an active tile or of moving the active tile to a location of the inactive tile;
    update the active portion of the layout template by:
        swapping the location of the active tile with the location of the inactive tile;
        activating the inactive tile; and
        deactivating the active tile;
    arrange the viewports according to the updated active portion of the layout template; and
    display, via the display user interface, the medical images in viewports in perspectives as indicated by indicators of corresponding tiles in the updated active portion of the layout template.

5. The computing device of claim 1, wherein the plurality of tiles include a volume rendering tile, and a viewport at a location corresponding to the volume rendering tile is configured to display a volume rendering of the medical images.

6. The computing device of claim 1, wherein the control user interface and the display user interface are provided on separate computing devices.

7. The computing device of claim 1, wherein the second display screen is separate from the first display screen.

8. A computer-enabled system for controlling a layout of displaying medical images in a plurality of render views, comprising:
    a first display screen;
    a second display screen;
    a control user interface displayed on said first display screen and configured to control the layout of displaying the medical images in the plurality of render views in the second display screen, said control user interface including a menu listing one or more layout templates and a layout template selected by a user from the one or more layout templates, the layout template having a plurality of tiles, each tile having an indicator of a render view, wherein the render view is a perspective in which one of the medical images will be displayed, and the layout template does not display the medical images;

a display user interface displayed on said second display screen and configured to display the same medical images in a plurality of perspectives, said display user interface being in communication with said control user interface and including a plurality of viewports arranged according to said layout template, and each viewport configured to display one of the same medical images in a perspective as indicated by a perspective indicator of a corresponding tile; and a layout control computing device comprising at least one processor electrically coupled to at least one memory device, said layout control computing device being in communication with said first display screen, said second display screen, said control user interface, and said display user interface, and said at least one processor programmed to:

receive, from said control user interface, a command by the user of moving a first tile to a location of a second tile in the layout template;

update said layout template by swapping a location of said first tile with the location of said second tile in response to the command;

instruct to arrange said viewports of the display user interface according to said updated layout template; and instruct to display, by said display user interface, the same medical images in said rearranged viewports in perspectives as indicated by perspective indicators of corresponding tiles in said updated layout template.

9. The system of claim 8, wherein said at least one processor is further programmed to:

receive, from said control user interface, a chosen layout template among said list of layout templates in the menu;

display the chosen layout template on the control user interface at a location different from a location of the menu;

arrange said viewports according to said chosen layout template; and display, by said display user interface, the medical images in said viewports in perspectives as indicated by indicators of corresponding tiles in said chosen layout template.

10. The system of claim 8, wherein said at least one processor is further programmed to:

display, via said control user interface, said layout template including an active portion and an inactive portion, wherein said active portion includes active tiles and said inactive portion includes an inactive tile;

arrange said viewports according to said active portion of said layout template; and display, via said display user interface, the medical images in said viewports in perspectives as indicated by indicators of corresponding tiles in said active portion of said layout template.

11. The system of claim 10, wherein said at least one processor is further programmed to:

receive, from said control user interface, a command by the user of moving an inactive tile to a location of an active tile or of moving said active tile to a location of said inactive tile;

update said active portion of said layout template by:
swapping the location of said active tile with the location of said inactive tile;
activating said inactive tile; and
deactivating said active tile;

arrange said viewports according to said updated active portion of said layout template; and display, via said display user interface, the medical images in viewports in perspectives as indicated by indicators of corresponding tiles in said updated active portion of said layout template.

12. The system of claim 8, wherein said plurality of tiles include a volume rendering tile, and a viewport at a location corresponding to said volume rendering tile is configured to display a volume rendering of the medical images.

13. The system of claim 8, wherein said control user interface and said display user interface are provided on separate computing devices.

14. The system of claim 8, wherein said second display screen is separate from said first display screen.

15. A computer-implemented method for controlling a layout of displaying medical images in a plurality of render views, said method comprising:

displaying, via a first display screen, a control user interface and configured to control the layout of displaying the medical images in the plurality of render views in a second display screen, wherein the control user interface includes a menu listing one or more layout templates and a layout template selected by a user from the one or more layout templates, and the layout template includes a plurality of tiles, each tile having an indicator of a render view, wherein the render view is a perspective in which one of the medical images will be displayed, and the layout template does not display the medical images;

displaying, via a second display screen, a display user interface configured to display the same medical images in a plurality of perspectives, wherein the display user interface includes a plurality of viewports arranged according to the layout template, and each viewport is configured to display one of the same medical images in a perspective as indicated by a perspective indicator of a corresponding tile;

receiving, from the control user interface, a command by the user of moving a first tile to a location of a second tile in the layout template;

updating the layout template by swapping a location of the first tile with the location of the second tile in response to the command;

arranging the viewports of the display user interface according to the updated layout template; and displaying, via the display user interface, the same medical images in the rearranged viewports in perspectives as indicated by perspective indicators of corresponding tiles in the updated layout template.

16. The method of claim 15, further comprising:

receiving, from the control user interface, a chosen layout template among the list of layout templates in the menu;

display the chosen layout template on the control user interface at a location different from a location of the menu;

arranging the viewports according to the chosen layout template; and displaying, by the display user interface, the medical images in the viewports in perspectives as indicated by indicators of corresponding tiles in the chosen layout template.

17. The method of claim 15, further comprising:

displaying, via the control user interface, the layout template including an active portion and an inactive portion, wherein the active portion includes active tiles and the inactive portion includes an inactive tile;

arranging the viewports according to the active portion of the layout template; and displaying, via the display user interface, the medical images in the viewports in perspectives as indicated by indicators of corresponding tiles in the active portion of the layout template.

18. The method of claim 17, further comprising:

receiving, from the control user interface, a command by the user of moving an inactive tile to a location of an active tile or of moving the active tile to a location of the inactive tile;

updating the active portion of the layout template by:
swapping the location of the active tile with the location of the inactive tile;
activating the inactive tile; and
deactivating the active tile;

arranging the viewports according to the updated active portion of the layout template; and displaying, via the display user interface, the medical images in viewports in perspectives as indicated by indicators of corresponding tiles in the updated active portion of the layout template.

19. The method of claim 15, wherein the plurality of tiles include a volume rendering tile, said method further comprising:

displaying, via a viewport at a location corresponding to the volume rendering tile, a volume rendering of the medical images.

20. The method of claim 15, wherein the control user interface and the display user interface are provided on separate computing devices.

* * * * *